US005279568A

United States Patent [19]

Cater

[11] Patent Number: 5,279,568

[45] Date of Patent: Jan. 18, 1994

[54] PHARMACEUTICAL PUMP DISPENSER FOR FLUID SUSPENSIONS AND FLUID MIXTURES

[75] Inventor: Miro S. Cater, Newtown, Conn.

[73] Assignee: Spruhventile GmbH, Wyhl am Kaiserstuhl, Fed. Rep. of Germany

[21] Appl. No.: 54,259

[22] Filed: Apr. 30, 1993

[51] Int. Cl.[5] ........................ A61M 1/00; A61M 37/00

[52] U.S. Cl. .................................... 604/152; 604/131; 222/321; 222/451

[58] Field of Search ............... 604/131, 135, 152, 187; 222/321, 383, 385, 451

[56] References Cited

U.S. PATENT DOCUMENTS

| | | | |
|---|---|---|---|
| 3,399,836 | 9/1968 | Pechstein | 222/321 |
| 3,640,470 | 2/1972 | Susuki et al. | 222/321 |
| 4,051,983 | 10/1977 | Anderson | 222/321 |
| 4,274,560 | 6/1981 | Cater | 222/321 |
| 5,038,965 | 8/1991 | Cater | 222/321 |
| 5,083,682 | 1/1992 | Cater | 222/321 |
| 5,147,073 | 9/1992 | Cater | 222/321 |
| 5,217,148 | 6/1993 | Cater | 222/321 |

*Primary Examiner*—John G. Weiss

[57] ABSTRACT

A finger actuated pump dispenser employs a first upper hollow vertical cylinder with a first diameter and open upper and lower ends and a second lower hollow vertical cylinder with a second and smaller diameter and a closed lower end with a central opening. The lower end of the first cylinder is joined to an open upper end of the second cylinder. The inner wall of the second cylinder has a horizontal annular recess. A first vertical hollow piston has openings in top and bottom ends and extends slidably above and within the cylinders. The first piston has an enlargement intermediate upper and lower ends peripherally engaging and defining a first unbroken seal with the inner surface of the first cylinder. The first piston has a lower section extending downward from the enlargement to its lower end, the lower section having an outer diameter slightly less than the diameter of the second cylinder. A second vertical piston peripherally engages and defines a second seal with the inner surface of the second cylinder. The second seal is unbroken except when the second piston is aligned with and spaced from the annular recess. A vertical stem is disposed slidably within the first piston and is secured at its lower end to the upper end of the said second piston. The stem is longer than the first piston so that there is always a vertical separation between the lower end of the first piston and the lower end of the stem. A spring extends within the second cylinder between its lower end and the lower end of the second piston.

10 Claims, 2 Drawing Sheets

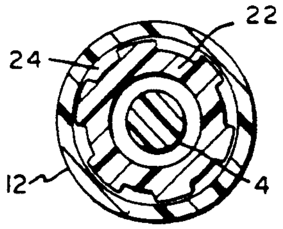
FIG. 5
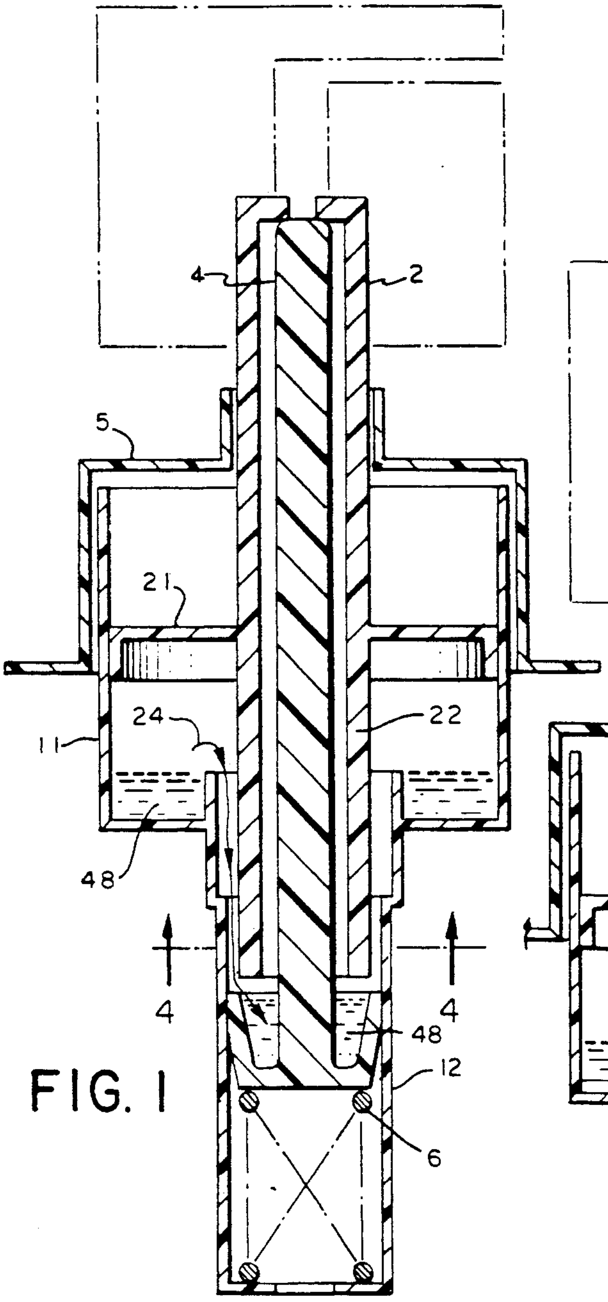
FIG. 1
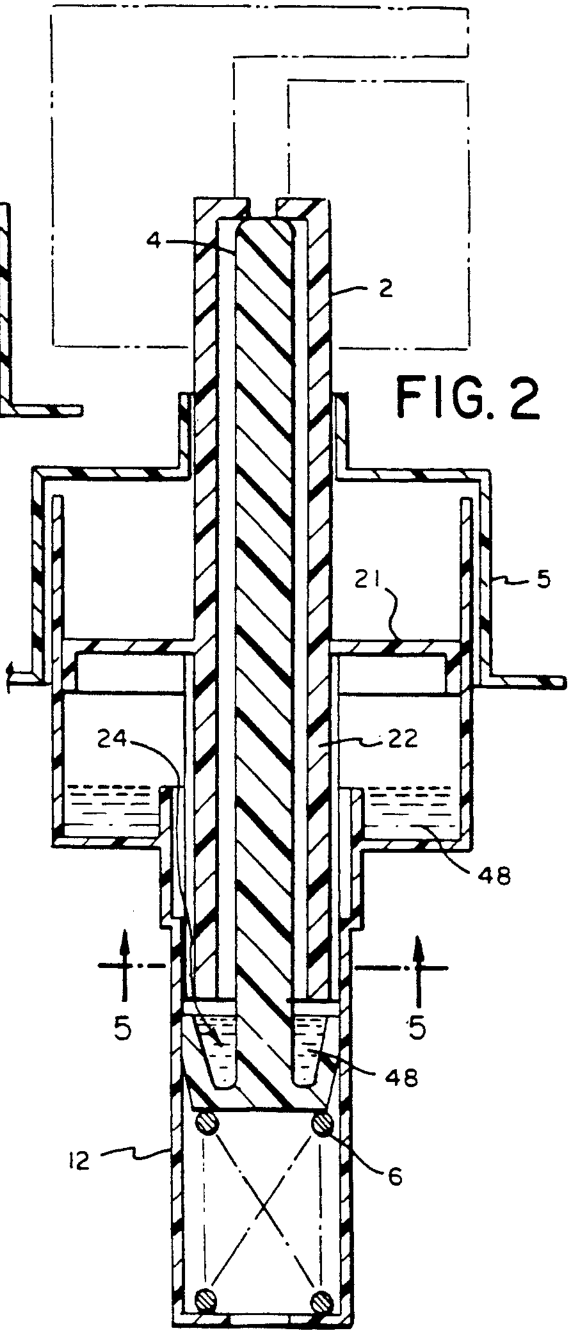
FIG. 2
FIG. 4
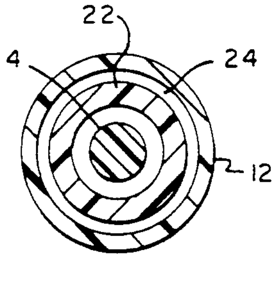

PHARMACEUTICAL PUMP DISPENSER FOR FLUID SUSPENSIONS AND FLUID MIXTURES

BACKGROUND OF THE INVENTION

Pump dispensers for dispensing pharmaceutical products in fluid form must deliver prescribed dosages with high accuracy.

Some pharmaceutical products are formulated as suspensions of particulate matter in fluids or as mixtures of liquids of different densities.

When pharmaceutical pump dispensers are used to dispense such formulations, the solids and similarly the higher density fluids tend to settle to the bottom of the dispenser pump chamber. To prevent improper delivery of the product, the user is instructed to actuate the dispenser several times before use in order to assure proper suspension or proper mixture. However, the user may fail to follow the instructions and the formulation may be delivered improperly, with unpleasant and even dangerous results.

The present invention is directed toward a new type of pharmaceutical dispenser for fluid suspensions or mixtures of fluids of different densities in which a first actuation of the dispenser automatically mixes the precipitate and fluid or fluids of different densities and produces and dispenses a proper fluid suspension or mixture without burdening the user with instructions which may not be followed.

SUMMARY OF THE INVENTION

Accordingly, it is an object of the present invention to provide a new and improved pharmaceutical dispenser for dispensing fluid suspensions or mixtures of fluids of different densities immediately without requiring the user to actuate the dispenser several times before use.

Another object is to provide a new and improved pharmaceutical dispenser of the character indicated wherein particulate matter and fluid or fluids of different densities are automatically mixed to produce the desired suspension or fluid mixture during actuation and wherein the suspension or mixture is automatically and properly dispensed.

These and other objects and advantages of this invention will either be explained or will become apparent hereinafter.

In accordance with the principles of this invention, a finger actuated pump dispenser employs a first upper hollow vertical cylinder with a first diameter and open upper and lower ends and a second lower hollow vertical cylinder with a second and smaller diameter and a closed lower end with a central opening. The lower end of the first cylinder is joined to an open upper end of the second cylinder. The inner wall of the second cylinder has a horizontal annular recess.

A first vertical hollow piston has openings in top and bottom ends and extends slidably above and within the cylinders. The first piston has an enlargement intermediate upper and lower ends peripherally engaging and defining a first unbroken seal with the inner surface of the first cylinder. The first piston has a lower section extending downward from the enlargement to its lower end, the lower section having an outer diameter slightly less than the diameter of the second cylinder. As will be explained in more detail hereinafter, the outer surface of the lower section can be smooth or can have grooves therein which can be vertical or pitched helical grooves.

A second vertical piston peripherally engages and defines a second seal with the inner surface of the second cylinder, the second seal being unbroken except when the second piston is aligned with and spaced from the annular recess. The second piston has upper and lower ends.

A vertical stem is disposed slidably within the first piston and has upper and lower ends. The stem is secured at its lower end to the upper end of the said second piston. The stem is longer than the first piston so that there is always a vertical separation between the lower end of the first piston and the lower end of the stem.

A spring extends within the second cylinder between its lower end and the lower end of the second piston.

The open upper end of the first piston and the upper end of the stem together define an outlet port. When the upper end of the stem engages the open upper end of the first piston, the outlet port is closed. When the upper end of the stem is spaced below the upper end of the first piston, the outlet port is open.

The second piston and the annular recess together define an inlet port. When the periphery of the second piston is aligned with and spaced from the recess, the inlet port is open. Otherwise the inlet port is closed.

In use, a collar closes off the top of the upper cylinder and is provided with a central opening through which the first piston extends. The collar is usually surrounded by a cup which attaches the dispenser to a container. The top opening in the first piston communicates with the discharge path of a top mounted actuator.

Initially, the upper cylinder is filled with either a fluid suspension wherein the particulate matter has settled to the bottom of the upper cylinder or is filled with fluids of different densities wherein the fluid of heaviest density has settled to the bottom of the upper cylinder. The outlet port is closed. When the actuator is depressed, the first piston, stem and second piston travel downward together and the outlet port remains closed. When the second piston passes the recess, the inlet port is closed. Since the fluid is incompressible, as the first piston, stem and second piston continue to travel downward, the fluid is displaced from the larger upper cylinder into the lower smaller cylinder via the narrow space between the outer surface of the lower section of the first piston and the inner wall of the lower cylinder. This action causes the second piston and stem to move downwardly with respect to the first piston, opening the outlet port. The fluid is forced upwardly between the first piston and stem and through the outlet port for discharge along the actuator discharge path.

When the liquid consists of fluids of different but similar densities, the outer surface of the lower section of the piston is smooth. Since the outer diameter of the lower section of the piston is only slightly smaller than the diameter of the second cylinder, the fluids are forced through this small separation with considerable force, producing a complete mixing action of the fluids so that the proper product is produced and dispensed.

When the densities of the fluids are substantially different, the mixing action produced when the outer surface of the lower section is smooth is sometimes insufficient. To overcome this problem, a plurality of spaced vertical grooves are formed in the otherwise smooth outer surface of the lower section. The liquids to be mixed are forced downwardly through the grooves, further confining the fluids and increasing the force exerted on the fluids as required to provide complete mixing of the fluids.

When the liquid consists of fluid and particulate matter, a plurality of pitched helical grooves are formed in the otherwise smooth outer surface of the lower section. The number and pitch of the grooves is dependent upon the density of the particulate and the size of the particles relative to the amount of fluid required. The helical shape lengthens the path traversed by the mixture of particulate and fluid as it is forced downwardly within the grooves, again producing a complete mixing action so that the proper product is produced and dispensed. The separation between the outer diameter of the lower section of the piston and the diameter of the second cylinder is determined by the size of the individual particles in the particulate matter to insure that the movement of these particles is confined to the helical grooves.

The first piston can be provided with one or more slots disposed in the lower section and interconnecting the interior of the second cylinder with the space between the first cylinder and the stem. This arrangement, as will be explained in more detail hereinafter, provides an additional mixing action.

BRIEF DESCRIPTION OF THE DRAWINGS

FIG. 1 shows a vertical cross sectional view, in simplified diagramatic form, a dispenser in accordance with the invention as adapted for mixing fluids of different but similar densities.

FIG. 2 is a horizontal cross section of a modification of the structure of FIG. 1 as adapted for mixing fluids of substantially different densities.

FIG. 4 is a horizontal cross section taken along line A—A in FIG. 1.

FIG. 5 is a horizontal cross section taken along line A—A in FIG. 2.

DETAILED DESCRIPTION OF PREFERRED EMBODIMENTS

Figure 3:
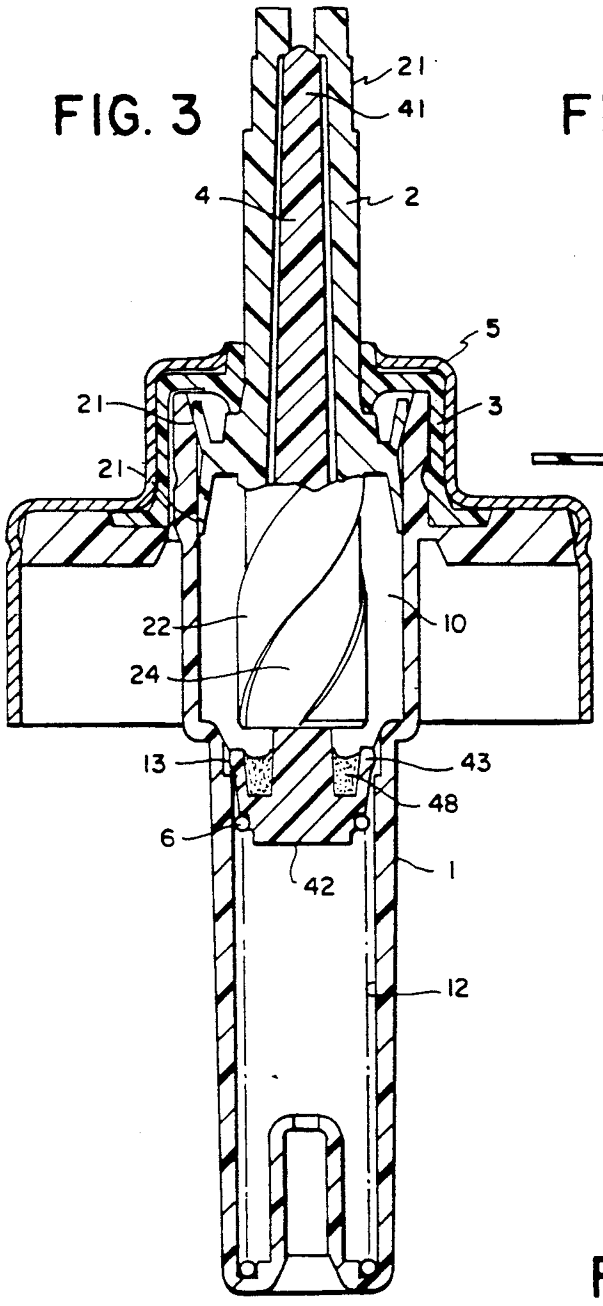
FIG. 3 shows a more detailed vertical cross sectional view of a dispenser in accordance with the invention as adapted for mixing fluid and particulate precipitated matter.

Referring first to FIGS. 1 and 4, a finger actuated pump dispenser employs a first upper hollow vertical cylinder 11 with a first diameter and open upper and lower ends and a second lower hollow vertical cylinder 12 with a second and smaller diameter and a closed lower end with a central opening. The purpose of the central opening is to allow the fluid mixture, which originally is in the container to which the dispenser is inserted, to be drawn out of the container by the dispenser to dispense the mixture. The lower end of the first cylinder is joined to an open upper end of the second cylinder. The inner wall of the second cylinder has a horizontal annular recess 13.

A first vertical hollow piston 2 having a top opening 25 and a bottom opening 24 extends slidably above and within the cylinders. The first piston has an enlargement 21 intermediate its ends peripherally engaging and defining a first unbroken seal with the inner surface of the first cylinder. Piston 2 has a lower extension 22 extending between the enlargement of the open bottom end of this piston. The outer surface of extension 22 is smooth. The outer diameter of extension 22 is only slightly smaller than the inner diameter of cylinder 12.

A second vertical piston 43 is disposed slidably within the second cylinder. The outer periphery of the second piston peripherally engages the inner surface of the second cylinder, forming a second seal therewith except when the second piston is aligned with and spaced from the annular recess 13. The second piston and the recess define an inlet port which is open when the piston is aligned with and spaced from the recess and is otherwise closed.

A vertical stem 4 is disposed slidably within the first piston and is spaced therefrom. The stem is longer than the first piston and always extends below the bottom opening in piston 2. The bottom end of the piston is secured to the upper end of piston. The outer surface 41 of stem 4 is smooth.

A spring 6 extends within the second cylinder between its lower end and the lower end of the second piston. Spring 6 is depressed during the down stroke of the pistons and expands during the following upstroke to return the pistons to the initial non-activated position. A collar 5 closes off the top of the upper cylinder and is provided with a central opening through which the first piston extends. The collar is usually surrounded by a cup which attaches the dispenser to a container. The top opening 25 in the first piston communicates with the discharge path of the top mounted actuator 8.

The upper end of piston 2 with opening 25 and the upper end of the stem forms an outlet port. The outlet port is closed when the upper end of the stem engages and closes opening 25. When the upper end of the stem is disposed below and out of engagement with opening 25, the outlet port is open.

Initially, the upper cylinder is filled with liquid and defines a pump chamber. The liquid is constituted by two or more fluids of different densities. The lower density fluid has settled to the bottom of the pump chamber. The outlet port is closed. When the actuator is depressed, the first piston, stem and second piston travel downward compressing spring 6. When the second piston passes the recess, the inlet port is closed.

Since the liquid is incompressible, as the first piston, stem and second piston continue to travel downward, the liquid is displaced from the larger upper cylinder 11 into the lower smaller cylinder via the narrow region between the lower section of the first piston and the inner wall of the smaller cylinder. Since the region is so narrow, the forces on the liquid produce thorough and complete mixing of fluids of similar but different densities. These forces also cause the second piston and the stem to move downwardly with respect to the first piston, opening the outlet port. The fluids so mixed pass through channel 41 between the stem and the first piston out of the open port, and the mixture of fluids is discharged through the actuator. The pressure on the actuator is then released, and the compressed spring 6 expands and returns the pistons to the non-actuated position. The compressed and expanded positions of the spring are shown in FIGS. 2 and 3 respectively.

As shown in FIGS. 2 and 5, the outer surface of the lower extension of the first piston is provided with a plurality of equidistantly spaced vertical grooves 24. Fluids of substantially different densities are not confined to the entire region between the lower section of the first piston and the wall of the inner cylinder, but instead are further confined in the vertical grooves. This arrangement produces the additional mixing forces required.

When the liquid to be dispensed consists of fluid and particulate matter, the outer surface of the lower section of the first piston should have one or more helical grooves, as shown in detail in FIG. 3.

The components of the dispenser shown in FIG. 3 which are the same as the components of the dispenser shown in FIG. 1 are identified by the same numbers. However, the outer surface of the lower section 22 of piston 2 shown in FIG. 2 has a plurality of helical grooves 54. In addition, the upper end of the second piston 43 has a circular recess 48. This recess defines the lowest region of the pump chamber, and the particulate matter will be deposited therein. Upon actuation in the same manner as previously described, the fluid will swirl downward along the grooves 24 with considerable force and be drawn into the sediment in recess 48. When the outlet port is opened, a mixture of fluid and lifted solids continues to spin which traveling toward the outlet port via the conduit formed between the first piston and the stem.

The number of grooves and the pitch thereof is determined by the density of the particulate and the size of the particles relative to the amount of fluid employed. If the particulate is not too dense and the particle sizes are sufficiently small, the structure shown in FIGS. 2 and 5 can be used in place of the structure in FIG. 3.

Figure 6:
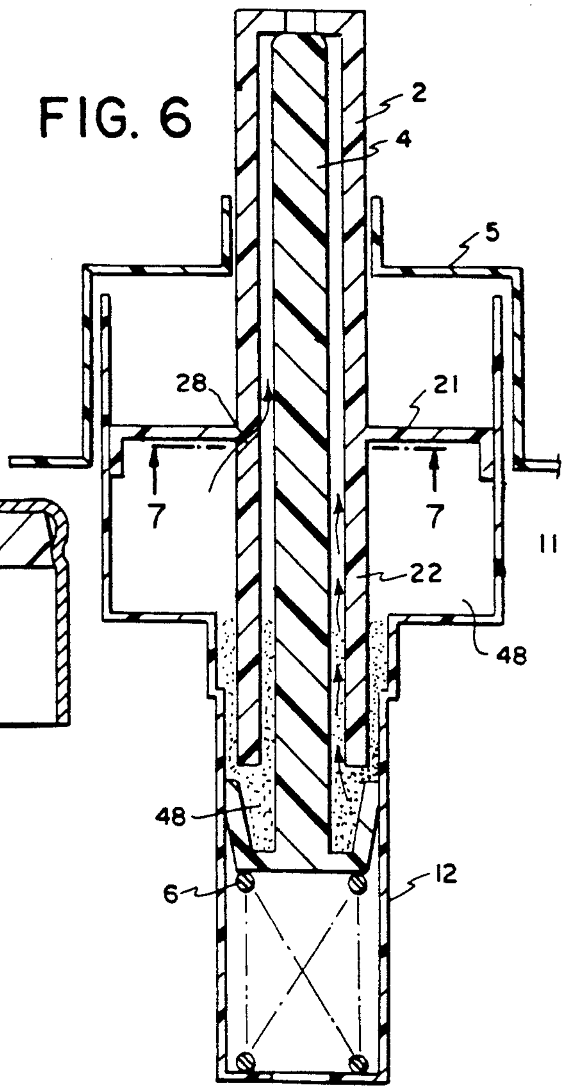
FIG. 6 is a horizontal cross section of a modification of the structure shown in FIG. 3 which provides an additional mixing action.
Figure 7:
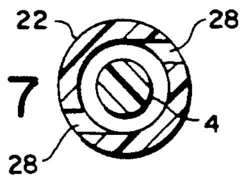
FIG. 7 is a horizontal cross section taken along line A—A in FIG. 6.

As shown in FIGS. 6 and 7, the structure shown in FIG. 3 can be modified by inserting least one slot 28. Two oppositely disposed slots are shown in FIGS. 6 and 7 interconnecting the interior of the second cylinder with the space between the first piston and the stem. While not shown, the same slot or slots can be used in the embodiment shown in FIG. 2. In either embodiment, the fluid in the interior of the second cylinder is mixed with the mixture of fluids or fluid and particulate being discharged through the space between the first piston and the stem, thus providing an enhanced mixing action.

While the invention has been disclosed with particular reference to the drawings and detailed description, the protection sought is to be limited only by the terms of the claims which follow.

What is claimed is:

1. A finger actuated pump dispenser comprising:

a first upper hollow vertical cylinder with a first diameter and open upper and lower ends;

a second lower hollow vertical cylinder with a second and smaller diameter and a closed lower end with a central opening, the lower end of the first cylinder being joined to an open upper end of the second cylinder, the inner wall of the second cylinder having a horizontal annular recess;

a first vertical hollow piston having openings in top and bottom ends and extending slidably above and within the cylinders, the first piston having an enlargement intermediate upper and lower ends peripherally engaging and defining a first unbroken seal with the inner surface of the first cylinder, the first piston having a lower section extending downward from the enlargement to its lower end, the lower section having an outer diameter slightly less than the diameter of the second cylinder;

a second vertical piston peripherally engaging and defining a second seal with the inner surface of the second cylinder, the second seal being unbroken except when the second piston is aligned with and spaced from the annular recess, the second piston having upper and lower ends;

a vertical stem disposed slidably within the first piston and having upper and lower ends, and secured at its lower end to the upper end of the said second piston, the stem being longer than the first piston so that there is always a vertical separation between the lower end of the first piston and the lower end of the stem; and a spring extending within the second cylinder between its lower end and the lower end of the second piston.

2. The dispenser of claim 1 further including at least one slot in the lower section of the first cylinder which extends between the interior of the second cylinder and the space between the first piston and the stem.

3. The dispenser of claim 2 containing two oppositely disposed slots.

4. The dispenser of claim 1 wherein the upper end of the stem is closed, the upper end of the stem and the upper end of the first piston defining an outlet port which is closed when these two upper ends are engaged in contact with each other and which is open when these two ends are separated.

5. The dispenser of claim 4 wherein the second seal defines an inlet port which is closed when the second seal is unbroken and which is open when the second seal is broken.

6. The dispenser of claim 5 wherein the outer surface of the lower extension of the first piston is provided with a plurality of spaced downwardly extending grooves.

7. The dispenser of claim 6 wherein the grooves are vertical.

8. The dispenser of claim 7 wherein the grooves are pitched helical grooves.

9. The dispenser of claim 8 wherein the upper end of the second piston has a circular recess.

10. The dispenser of claim 9 wherein the recess surrounds the lower end of the stem.

* * * * *